United States Patent
Sato

(10) Patent No.: US 9,285,341 B2
(45) Date of Patent: Mar. 15, 2016

(54) APPARATUS MONITORING FOR ABNORMALITIES

(75) Inventor: Tomoyoshi Sato, Tsukúba (JP)

(73) Assignee: ATONARP INC., Hachioji-Shi, Tokyo (JP)

( * ) Notice: Subject to any disclaimer, the term of this patent is extended or adjusted under 35 U.S.C. 154(b) by 0 days.

(21) Appl. No.: 14/343,069

(22) PCT Filed: Sep. 4, 2012

(86) PCT No.: PCT/JP2012/005597
§ 371 (c)(1),
(2), (4) Date: Mar. 26, 2014

(87) PCT Pub. No.: WO2103/035307
PCT Pub. Date: Mar. 14, 2013

(65) Prior Publication Data
US 2014/0284479 A1 Sep. 25, 2014

(30) Foreign Application Priority Data
Sep. 6, 2011 (JP) .................................. 2011-194424

(51) Int. Cl.
*G01N 27/62* (2006.01)
*G01M 5/00* (2006.01)

(52) U.S. Cl.
CPC ............ *G01N 27/622* (2013.01); *G01M 5/0025* (2013.01); *G01M 5/0033* (2013.01); *G01M 5/0075* (2013.01); *G01N 27/62* (2013.01)

(58) Field of Classification Search
USPC .............................................. 250/290, 336.1
See application file for complete search history.

(56) References Cited

U.S. PATENT DOCUMENTS 5,362,568 A   11/1994 Dietz et al.
6,107,624 A   8/2000 Doring et al.
(Continued)

FOREIGN PATENT DOCUMENTS

EP   1 582 868 A1   10/2005
JP   47-8745 A   5/1972
(Continued)

OTHER PUBLICATIONS

Notification of Transmittal of Copies of Translation of the International Preliminary Report on Patentability (Chapter I or Chapter II)(PCT/IB/338) and International Preliminary Report on Patentability (Form PCT/IB/373) and Written Opinion of the International Searching Authority for International (Translation)(Form PCT/ISA/237) issued on Mar. 20, 2014, in corresponding International Application No. PCT/JP2012/005597. (6 pages).

(Continued)

*Primary Examiner* — Phillip A Johnston
*Assistant Examiner* — Hsien Tsai
(74) *Attorney, Agent, or Firm* — Buchanan Ingersoll & Rooney PC

(57) ABSTRACT

There is provided a monitoring apparatus that monitors abnormalities in a system including a plurality of components or products. The plurality of components or products respectively include a plurality of types of microcapsules that release, due to specific causes, a plurality of marker chemical substances respectively, the marker chemical substances having respectively different ion mobilities. The monitoring apparatus includes an ion mobility sensor that detects the plurality of marker chemical substances. By detecting the marker chemical substances, the monitoring apparatus is capable of identifying the occurrence of an abnormal state, the type of abnormal state, the occurrence location, the extent of the abnormal state, and the like.

16 Claims, 3 Drawing Sheets

(56) References Cited

U.S. PATENT DOCUMENTS

| | | | |
|---|---|---|---|
| 8,347,685 B1 * | 1/2013 | Chu et al. | 73/1.06 |
| 2008/0191132 A1 | 8/2008 | Boyle et al. | |
| 2009/0325300 A1 * | 12/2009 | Clift et al. | C12Q 1/04 436/57 |
| 2010/0080351 A1 | 4/2010 | Hession-Kunz et al. | |
| 2010/0185143 A1 * | 7/2010 | Uhland et al. | A61M 5/16836 604/67 |
| 2010/0308995 A1 | 12/2010 | Goto et al. | |
| 2011/0006196 A1 | 1/2011 | Boyle et al. | |

FOREIGN PATENT DOCUMENTS

| | | | |
|---|---|---|---|
| JP | H05-018831 A | 1/1993 | |
| JP | 7-134071 A | 5/1995 | |
| JP | 7-167733 A | 7/1995 | |
| JP | 10-267866 A | 10/1998 | |
| JP | 2002-371191 A | 12/2002 | |
| JP | 2008-508693 A | 3/2008 | |
| JP | 2009-187227 A | 8/2009 | |
| JP | 2011-094975 A | 5/2011 | |
| WO | WO 2006/013396 A2 | 2/2006 | |
| WO | 2010/136775 A2 | 12/2010 | |

OTHER PUBLICATIONS

International Search Report (PCT/ISA/210) mailed on Oct. 2, 2012, by the Japanese Patent Office as the International Searching Authority for International Application No. PCT/JP2012/005597.

Written Opinion (PCT/ISA/237) mailed on Oct. 2, 2012, by the Japanese Patent Office as the International Searching Authority for International Application No. PCT/JP2012/005597.

Search Report and Written Opinion issued on Mar. 17, 2015, by the Intellectual Property Office of Singapore in corresponding Singaporean Application No. 2014008247. (16 pages).

Hill et al., "Ion Mobility Spectrometry," Analytical Chemistry, (Dec. 1, 1990), vol. 62, No. 23, pp. 1201A-1209A, 9 pages.

The extended European Search Report issued on Oct. 6, 2015, by the European Patent Office in corresponding European Patent Application No. 12829842.9-1557. (9 pages).

* cited by examiner

APPARATUS MONITORING FOR ABNORMALITIES

TECHNICAL FIELD

The present invention relates to a monitoring apparatus using marker substances that are detectable by an ion mobility sensor.

BACKGROUND ART

Japanese Laid-Open Patent Publication No. 2009-187227 discloses the provision of an odor-generating alarm apparatus and an abnormal state warning method that are highly safe and have a very clear effect in attracting attention. The odor-generating alarm apparatus in this document includes an odor substance vessel, a driving unit, a detector, and a circuit as a control unit. The odor substance vessel stores an odor substance. The concentration of the odor substance in air at which the odor is so strong as to become unbearable for humans is lower that the no observed effect concentration of the odor substance. The driving unit releases the odor substance from the odor substance vessel. The detector detects the occurrence of an abnormal state and outputs a detection signal. The control unit receives input of the detection signal from the detector and has the driving unit release the odor substance in accordance with the detection signal.

Japanese Patent Publication No. 2008-508693 (International Publication No. WO2006/013396) discloses an apparatus that measures physical phenomena based on differences in ion mobility between substances. In particular, such publication discloses an ion mobility spectrometer with an ion filter in the form of at least one ion channel that includes a plurality of electrodes. With this ion mobility spectrometer, it is possible for the filler to selectively input ion types according to the potential applied to the conductive layer that changes over time. Such potential has a drive electric field component and a transverse electric field component, and in a preferred embodiment, the respective electrodes contribute to the generation of both the drive electric field component and the transverse electric field component. Such device can be used even without a drift gas flow.

DISCLOSURE OF THE INVENTION

When an abnormal state has occurred, the odor-generating alarm apparatus disclosed in Japanese Laid-Open Patent Publication No. 2009-187227 informs people of the occurrence of the abnormal state by releasing an odor substance at a concentration where the odor is so strong as to become unbearable for humans. Even if the number of types of odors is increased, it is difficult to give an indication of what kind of abnormality has occurred and where. Also, even if it is possible to release a plurality of odors, if a plurality of odors are simultaneously released, it is difficult to determine what kind of abnormality has occurred.

One aspect of the present invention is an apparatus that monitors abnormalities in a system including a plurality of components or products. The plurality of components or products respectively include a plurality of types of capsules that release, due to specific causes, a plurality of marker chemical substances respectively, the marker chemical substances having respectively different ion mobilities. Also, the apparatus includes an ion mobility sensor that detects the plurality of marker chemical substances. The capsules (microcapsules) have a predetermined resistance to pressure (pressure resistance), for example, and are destroyed when a predetermined pressure or higher is applied. The capsules may also be capsules with predetermined resistance to heat (heat resistance), light resistance, weather resistance, or chemical resistance.

In this system, a cause to be monitored can be freely set by selecting the material, strength, and the like of the capsules. Also, the marker chemical substance that is released can be changed according to the monitored cause and changed according to the component or product to be monitored. Accordingly, identification of the monitored cause, and identification of a component or product to be monitored (which includes means of identification of a specific individual part, identification of an installed location, and the like) are possible by detecting a marker chemical substance using an ion mobility sensor.

Another aspect of the present invention is particles that generates a signals for use by an ion mobility sensor, including: a plurality of marker chemical substances with different ion mobilities: and a plurality of types of capsules (microcapsules) that encapsulate the plurality of marker chemical substances respectively and release, due to specific causes, the respective marker chemical substances. Such particles may be provided having been included in products or may be provided having been included in semifinished products, such as paints, resins, or members.

Yet another aspect of the present invention is a monitoring system including: a component or product to be monitored including the particles described above; and an ion mobility sensor that detects the plurality of marker chemical substances.

Yet another aspect of the present invention is a control method of an apparatus that monitors a system including a plurality of components or products for abnormalities (problems). The plurality of components or products respectively include a plurality of types of capsules that release, due to specific causes, a plurality of marker chemical substances respectively, the marker chemical substances having respectively different ion mobilities, and the monitoring apparatus includes an ion mobility sensor that detects the plurality of marker chemical substances. The control method includes determining, when the ion mobility sensor detects a marker chemical substance out of the plurality of marker chemical substances, a component or product related to the detected marker chemical substance out of the plurality of components or products.

DETAIL DESCRIPTION

Figure 1:
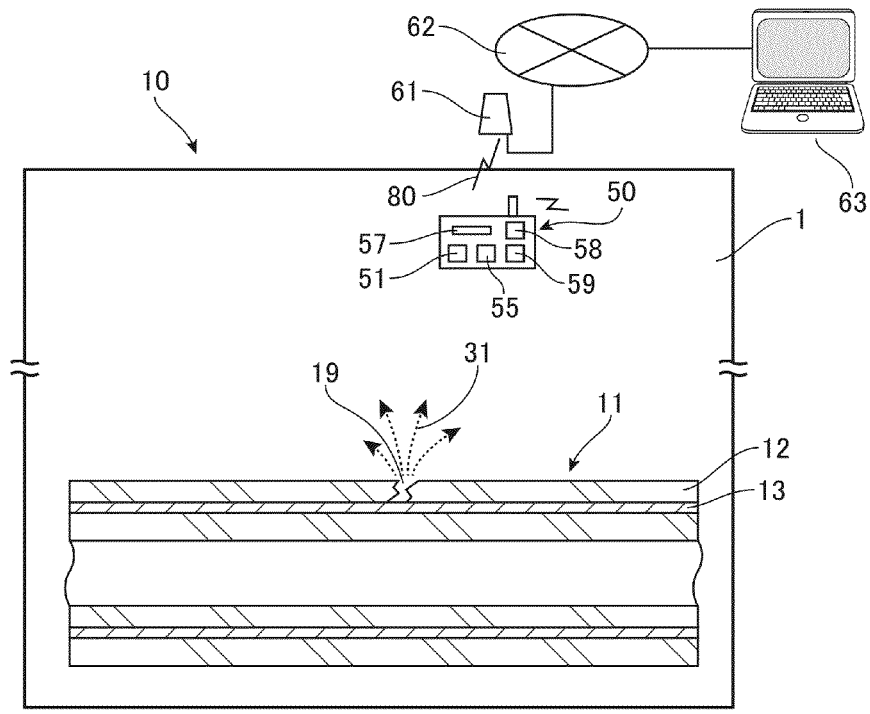
FIG. 1 shows an overview of a monitoring system.

FIG. 1 shows an overview of a monitoring system that uses particles that generate a signal or signals for an ion mobility sensor. Such monitoring system 10 monitors a monitored object (target) 11 that is disposed, installed, or assembled in an enclosed or semi-enclosed space 1 for the presence of damage. In this example, the monitored object 11 is a pipe and a monitoring layer 13 including particles is formed in the wall 12 of the pipe. The monitoring system 10 also includes a monitoring unit 50 that detects chemical substances (including molecules, compounds, compositions, and the like) that are released from the pipe 11 being monitored when an abnormality occurs.

The monitoring unit (monitoring apparatus, monitor) 50 includes a sampling pump 51 that samples the air inside the space 1, an ion mobility sensor 55 that measures or detects chemical substances included in the sampled gas, and a communication unit 57 that outputs a detection result via a means such as a wireless LAN. The monitoring unit 50 transmits information 80 on an abnormal state via a base station 61, for example, to a host connected to the Internet, for example a personal computer 63.

The monitoring unit 50 may also include a database 58 and a control unit (processor) 59 that determines an abnormal state based on information stored in the database 58. The database 58 includes information specifying the chemical substances to be monitored and information showing the relationship between components, products and causes to be monitored and the chemical substances. The database 58 and the function 59 that determines an abnormal state may be included at the host 63.

Figure 2:
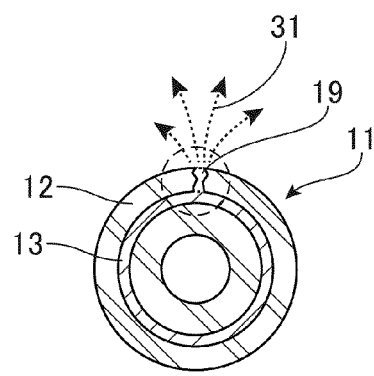
FIG. 2 is a cross-sectional view of a pipe being monitored.
Figure 3:
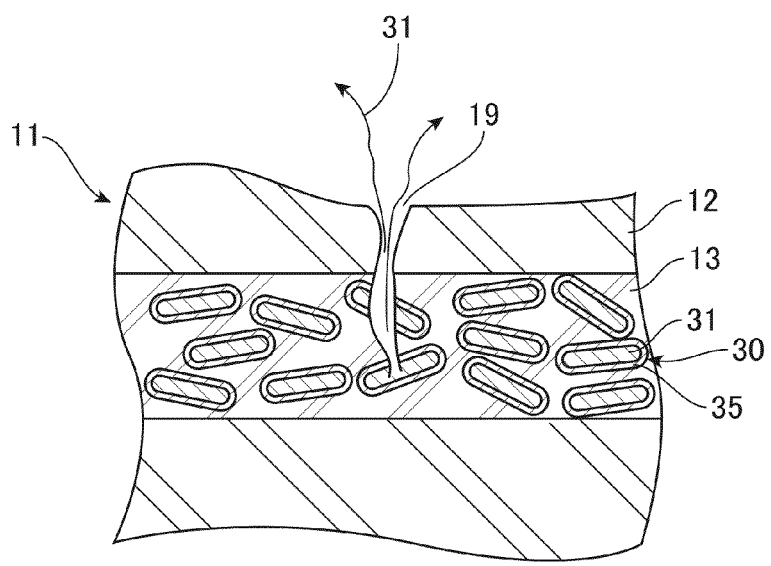
FIG. 3 shows an enlargement of a layer including particles that detect pressure.

FIG. 2 shows a cross section of the pipe 11 to be monitored. FIG. 3 shows an enlargement of the monitoring layer 13 including the particles 30. The particles 30 for signal generation include microcapsules 35 with a size of around 0.1 μm to 5 mm and a marker substance (chemical substance) 31 that is sealed inside the microcapsules 35. The marker substance 31 encapsulated in the microcapsules 35 is one (a type) of a large number of chemical substances detected by the ion mobility sensor 55 and a spectrum produced when such marker substance 31 is detected by the ion mobility sensor 55 is registered in the database 58 or the like.

As examples, FAIMS (Field Asymmetric Waveform Ion Mobility Spectrometry) or DIMS (Differential Ion Mobility Spectrometry) can be used as the ion mobility sensor 55. A different type of ion mobility sensor may also be used. The chemical substances that can be measured (detected) by a FAIMS are compounds, compositions, and molecules that can be ionized, the property whereby ion mobility is unique to each chemical substance is used, and a differential voltage (or "DV", "Dispersion Voltage", "Vd voltage", "electric field voltage Vrf", or "AC voltage", hereinafter simply "Vf") and a compensation voltage (or "CV", "compensation voltage", "DC voltage", hereinafter simply "Vc") are applied while causing such chemical substances to move in a buffer gas. By appropriately controlling the values of Vf and Vc, the detection target chemical substances that have been ionized will reach a detector and be detected as current values.

The microcapsules 35 are any out of a plurality of types of microcapsules including materials and/or wall films designed so that the fracture temperature and/or pressure ranges do not overlap each other. Although there are a number of methods for manufacturing the microcapsules 35, examples include interfacial polymerization and in situ microcapsules, with representative examples of microcapsules manufactured by such methods being polyurethane capsules that use polyvalent isocyanate and melamine-formaldehyde resin capsules. In the case of capsules made of polyurethane, both the polyvalent isocyanate and a polyhydroxy compound are melted at the same time into the oil phase, such substances are emulsified and dispersed in a protective colloid aqueous solution, the temperature is raised further, and a reaction occurs to form capsule walls. In the case of capsules made of melamine-formaldehyde resin, a melamine-formaldehyde prepolymer that is soluble in water is used. By adding such prepolymer solution to an O/W emulsion where an oil produced by melting a dye precursor has been emulsified and dispersed in a protective colloid aqueous solution and then heating and stirring in a weakly acidic region (with a pH of 3 to 6), polymer is deposited on the O/W interfaces to produce microcapsules. As the protective colloid, it is possible to use a colloid that functions as an acid catalyst that promotes a polycondensation reaction of the melamine-formaldehyde resin (as examples, a styrene sulfonic acid polymer, a copolymer of styrene and maleic anhydride, a copolymer of ethylene and maleic anhydride, gum arabic, and polyacrylic).

The materials and method of manufacturing the microcapsules are not limited to the above. Provided that the microcapsules are capable of sufficiently holding their content without being destroyed under pressure conditions and heating conditions that occur during storage or transportation before use and are microcapsules capable of being destroyed when subjected to heat or pressure under predetermined conditions so as to release the encapsulated chemical substance 31, there are no particular limitations and it is possible to use capsules manufactured using various known materials and methods of manufacturing.

If the microcapsules 35 are destroyed, damaged, dissolved, or caused to disappear under predetermined conditions, the particles 30 for generating a signal will release the specified chemical substance 31 that was encapsulated inside the microcapsules 35. Accordingly, by changing the type of chemical substance 31 according to the cause of destruction, and by detecting the chemical substance 31 released to the atmosphere, the monitoring unit 50 is capable of identifying the cause of destruction of the microcapsules 35.

In addition, it is also possible to prepare particles 30 where the microcapsules 35 are destroyed by the same cause but which include different types of chemical substances 31 and to set such particles 30 that include different types of chemical substances 31 in different members, in different equipment or at different locations. In such case, by detecting the chemical substance 31 that has been released to the atmosphere, the monitoring unit 50 is capable of identifying (specifying) the destroyed member, equipment, or location and the cause of destruction.

The monitoring layer 13 of the pipe 11 to be monitored may be a material including resin that includes the particles 30 or may be a member that includes the particles 30. If excessive pressure is applied to the pipe 11 or a shock is applied and a crack 19 is produced in the wall 12 of the pipe 11, excessive pressure will be applied to the particles 30 of the monitoring layer 13. If pressure equal to or larger than the withstand pressure of the microcapsules 35 is applied to the particles 30, the microcapsules 35 will be destroyed or damaged and the encapsulated (embedded or included) chemical substance 31 is released. On detecting the released chemical substance 31, the monitoring unit 50 identifies that the pipe 11 that is one of the targets of monitoring has been damaged and transmits information 80 including the occurrence of an abnormal state to the computer 63.

If particles 30 in which a different chemical substance 31 is encapsulated are included at a different location on the pipe 11 being monitored or in a second monitoring layer at a different location in the thickness direction, by detecting the chemical substance 31 released from the particles 30, the monitoring unit 50 is capable of obtaining information relating to the location where the crack 19 has occurred and/or the depth of the crack 19. Accordingly, the monitoring unit 50 provides information 80 that includes not only the cause of an abnormal state but also the location where the abnormal state has occurred and/or the extent of the damage due to the abnormal state to the computer 63.

Figure 4:
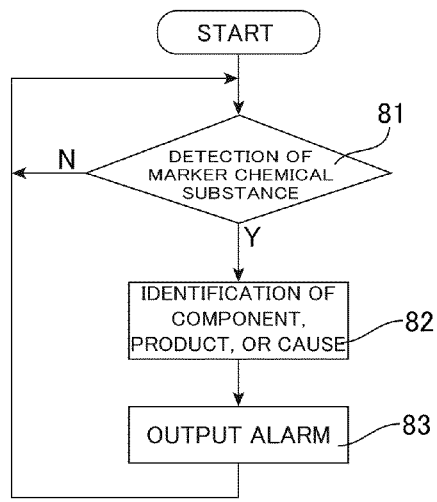
FIG. 4 is a flowchart showing a process that monitors for abnormalities using a monitoring system.

FIG. 4 shows a process of monitoring for an abnormal state using the monitoring system 10 by way of a flowchart. If, in step 81, the ion mobility sensor 55 of the monitoring unit 50 detects the chemical substance (compound, marker substance) 31 used as a marker, in step 82 the control unit 59 refers to the database 58 and identifies the component, product, or cause related to the marker chemical substance 31 that has been detected out of the components, products, or causes being monitored. Next, in step 83, an alarm is outputted and also information 80 that includes not only the occurrence of the abnormal state but also the type of abnormal state, occurrence location, and extent of the abnormal state is outputted to the host 63. Depending on the object monitored in the monitoring system 10 or the cause, the monitoring unit 50 may carry out appropriate processing such as forcibly stopping the operation of the apparatus or system including the component or product being monitored or the host 63 that has received the information 80 may carry out such processing.

Figure 5:
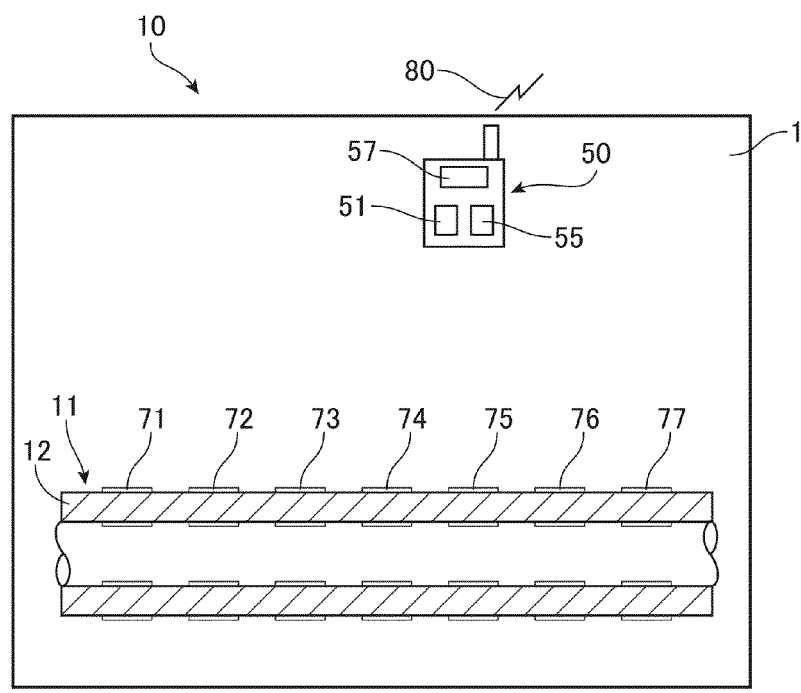
FIG. 5 is a different example of a monitoring system.

FIG. 5 shows a different example of a monitoring system. This monitoring system 10 also includes a pipe 11 that is to be monitored and is disposed in an enclosed space 1 and a monitoring unit 50. The pipe 11 being monitored is painted with a plurality of types of materials (semifinished products), for example paints 71 to 77. The paints 71 to 77 include particles 30 where respectively different types of chemical substances 31 are encapsulated in microcapsules 35 that have different melting temperatures.

Figure 6:
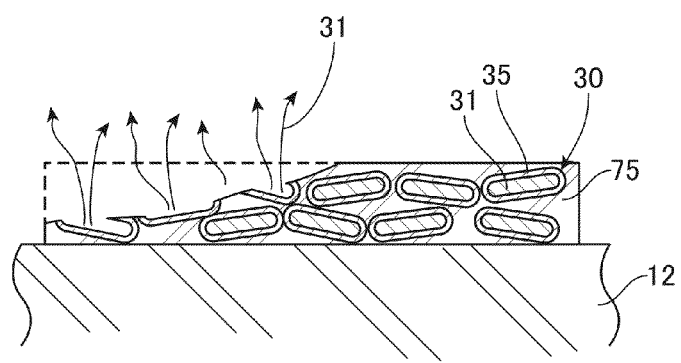
FIG. 6 shows an enlargement of paint including particles that detect temperature.

FIG. 6 shows a state where the paint 75 has melted as one example. It is desirable for the paints 71 to 77 to be paints with different resistance to heat. The paint 75 melts when the temperature in the vicinity of the pipe 11 reaches a predetermined temperature and the microcapsules 35 also melt. Accordingly, the chemical substance 31 encapsulated in the microcapsules 35 is released and by having the monitoring unit 50 identify the released chemical substance 31, it is possible to know the temperature on the inside or in the vicinity of the pipe 11. In addition, by preparing particles 30 that include microcapsules 35 with the same resistance to heat but which have different chemical substances 31 encapsulated in the microcapsules 35 and applying such particles 30 at different locations on the pipe 11, it is possible for the monitoring unit 50 to know the temperature reached by the pipe 11 and the locations where such temperature was reached along the pipe 11. Accordingly, the monitoring unit 50 is capable of transmitting the information 80 that includes not only the abnormal state but also the location and content of the abnormal state to the computer 63.

In this way, by combining the characteristics of the microcapsules 35 and the chemical substance 31 in which the microcapsules 35 are encapsulated in the particles 30 used for signal generation, it is possible to supply a signal (information) that, in addition to information relating to the environment in which the particles 30 are installed, specifies the location, the appliance or the member where the particles 30 are installed via the chemical substances 31 to the monitoring unit 50. Accordingly, even if the product, location, or the like being monitored cannot be visually seen from the monitoring unit 50, there is no room to install measuring equipment, or it is not possible to attach measuring equipment to the product or location, it is still possible for the monitoring unit 50 to acquire a signal showing an abnormal state via the chemical substances 31.

The microcapsules 35 for generating a signal are not limited to capsules with a predetermined resistance to pressure and resistance to heat. It is also possible to provide microcapsules 35 with certain weather resistance, light resistance, chemical resistance, and the like, and possible to detect the occurrence of abnormalities with various different conditions according to the combination of the particles 30 and the monitoring unit 50 equipped with the ion mobility sensor 55.

The monitoring unit 50 equipped with the ion mobility sensor 55 is not limited to a fixed device and may be mobile, such as a mobile terminal. By using the particles 30 for generating a signal, it is possible to positively and appropriately transmit the occurrence of an abnormal state to the monitoring unit 50. Also, aside from damage to equipment, when debris, dust, foreign matter, or the like is produced due to some kind of situation, if the particles 30 for generating a signal are included, it is possible to easily detect the presence of such debris or the like by detecting the chemical substances 31 released from the debris. Accordingly, it is possible to prevent the occurrence of a situation such as when foreign matter is mixed into food, from the outset.

The invention claimed is:

1. An apparatus that monitors abnormalities in a system including a plurality of components or products disposed in an enclosed or semi-enclosed space,
    wherein the plurality of components or products respectively includes a plurality of types of capsules, wherein each of the types of capsule releases a unique one of a plurality of marker chemical substances, and each type of capsule releases its unique marker chemical substance due to a specific predetermined cause, and each of the plurality of marker chemical substances has a unique spectrum,
    the apparatus comprises:
    a sensor that is capable of detecting the spectrums of the plurality of marker chemical substances by sampling air in the space,
    a database that includes information of a relationship among the unique spectrums of the plurality of marker chemical substances, the plurality of marker chemical substances, the plurality of components or products, and the specific predetermined cause associated with each of the plurality of marker chemical substances; and
    a unit that determines an abnormal state of one of the plurality of components or products based on the spectrum detected by the sensor, and the predetermined specific causes registered in the database.

2. The apparatus according to claim 1,
    wherein each of the plurality of types of capsules respectively has a predetermined resistance to pressure, resistance to heat, weather resistance, light resistance, or chemical resistance.

3. A control method of an apparatus that monitors a system including a plurality of components or products disposed in an enclosed or semi-enclosed space for abnormalities,
    wherein the plurality of components or products respectively includes a plurality of types of capsules, wherein each of the types of capsule releases a unique one of a plurality of marker chemical substances, and each type of capsule releases its unique marker chemical substance due to a specific predetermined cause, and each of the plurality of marker chemical substances has a unique spectrum , and the apparatus comprises:
    a sensor that is capable of detecting the spectrums of the plurality of marker chemical substances by sampling air in the space; and
    a database that includes information of a relationship among the unique spectrums of the plurality of marker chemical substances, the plurality of marker chemical substances, the plurality of components or products, and the specific predetermined cause associated with each of the plurality of marker chemical substances; and the control method comprises determining an abnormal state of one of the plurality of components or products based on the spectrum detected by the sensor, and the predetermined specific causes registered in the database.

4. A monitoring system comprising:

the apparatus according to claim 1; and the plurality of components or products disposed in the enclosed or semi-enclosed space, the air in the space being sampled by the apparatus and the plurality of components or products respectively include the plurality of types capsules that release, due to the respective predetermined abnormality, at least one of the plurality of marker chemical substances respectively, the plurality of marker chemical substances having respectively different spectrums.

5. The monitoring system according to claim 4, wherein the plurality of components or products include a paint, a resin or a member that includes at least one of the plurality of types of capsules.

6. A component or product including material that is one of the paint, the resin and the member described in claim 5.

7. A component or a product described in claim 1.

8. A paint, a resin or a member that includes at least one of the plurality of types of capsules according to claim 1.

9. The monitoring system of claim 4, wherein the at least one of the plurality of components or products disposed in the enclosed or semi-enclosed space is a pipe, and one of the plurality of types of capsules are encased in a monitoring layer formed in a wall of the pipe.

10. The monitoring system of claim 4, wherein the at least one of the plurality of components or products disposed in the enclosed or semi-enclosed space is a pipe, and one of the plurality of types of capsules are encased in a wall of the pipe such that when the wall is damaged the at least one of the plurality of marker chemical substances is released from the capsules.

11. The method of claim 3, wherein the at least one of the plurality of components or products disposed in the enclosed or semi-enclosed space is a pipe, and one of the plurality of types of capsules are encased in a monitoring layer formed in a wall of the pipe.

12. The method of claim 3, wherein the at least one of the plurality of components or products disposed in the enclosed or semi-enclosed space is a pipe, and one of the plurality of types of capsules are encased in a wall of the pipe such that when the wall is damaged the at least one of the plurality of marker chemical substances is released from the capsules.

13. The apparatus of claim 1, wherein the predetermined specific cause is pressure, and the abnormal state is destruction of a component or product installed at a certain location registered in the database.

14. The method of claim 3, wherein the predetermined specific cause is pressure, and the abnormal state is a destruction of a destruction of a component or product installed at a certain location registered in the database.

15. The apparatus of claim 1, wherein each of the plurality of marker chemical substances corresponds to a particular location of a component or a product, wherein the apparatus further includes a unit for identifying the location or part where the marker chemical released based on the relationship registered in the database.

16. The method of claim 3, wherein each of the plurality of marker chemical substances corresponds to a particular location of a component or a product, wherein the method further includes identifying the location or part where the marker chemical released based on the relationship registered in the database.

* * * * *